(12) United States Patent
Cheng et al.

(10) Patent No.: US 7,213,476 B2
(45) Date of Patent: May 8, 2007

(54) STACKABLE DIFFERENTIAL MOBILITY ANALYZER FOR AEROSOL MEASUREMENT

(75) Inventors: Meng-Dawn Cheng, Oak Ridge, TN (US); Da-Ren Chen, Creve Coeur, MO (US)

(73) Assignee: UT-Battelle, LLC, Oak Ridge, TN (US)

( * ) Notice: Subject to any disclaimer, the term of this patent is extended or adjusted under 35 U.S.C. 154(b) by 43 days.

(21) Appl. No.: 11/240,161

(22) Filed: Sep. 30, 2005

(65) Prior Publication Data

US 2006/0266132 A1 Nov. 30, 2006

Related U.S. Application Data

(60) Provisional application No. 60/685,933, filed on May 31, 2005.

(51) Int. Cl.
*G01N 15/00* (2006.01)
(52) U.S. Cl. .................................... 73/865.5
(58) Field of Classification Search ............... 73/865.5, 73/28.04, 863.21; 96/15, 17; 356/335, 336, 356/440
See application file for complete search history.

(56) References Cited

U.S. PATENT DOCUMENTS 6,230,572 B1 * 5/2001 Pui et al. ................. 73/863.21
6,639,671 B1 10/2003 Liu ............................ 356/336
6,787,763 B2 * 9/2004 De La Mora et al. ...... 250/287

OTHER PUBLICATIONS

Chen et al. "Design and evaluation of nanometer aerosol differential mobility analyzer (Nano-DMA)", J. Aerosol Sci., 1998, 29(5/6):497-200.
Seol et al. "A differential mobility analyzer with adjustable column length for wide particle-size-range measurements", J. Aerosol Sci., 2002, 33:1481-1492.

* cited by examiner

*Primary Examiner*—Hezron Williams
*Assistant Examiner*—Tamiko Bellamy
(74) *Attorney, Agent, or Firm*—Akerman Senterfitt; Neil Jetter; Eduardo J. Quinones

(57) ABSTRACT

A multi-stage differential mobility analyzer (MDMA) for aerosol measurements includes a first electrode or grid including at least one inlet or injection slit for receiving an aerosol including charged particles for analysis. A second electrode or grid is spaced apart from the first electrode. The second electrode has at least one sampling outlet disposed at a plurality different distances along its length. A volume between the first and the second electrode or grid between the inlet or injection slit and a distal one of the plurality of sampling outlets forms a classifying region, the first and second electrodes for charging to suitable potentials to create an electric field within the classifying region. At least one inlet or injection slit in the second electrode receives a sheath gas flow into an upstream end of the classifying region, wherein each sampling outlet functions as an independent DMA stage and classifies different size ranges of charged particles based on electric mobility simultaneously.

14 Claims, 12 Drawing Sheets

STACKABLE DIFFERENTIAL MOBILITY ANALYZER FOR AEROSOL MEASUREMENT

CROSS-REFERENCE TO RELATED APPLICATIONS

This application claims the benefit of and incorporates by reference in its entirety Provisional Application No. 60/685,933 filed on May 31, 2005.

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

FIELD OF THE INVENTION

The invention relates to methods and apparatus for sizing and classifying charged particle or ions based on differential mobility analysis.

BACKGROUND OF THE INVENTION

Particle size is a significant parameter for particles, which can be used to characterize the behavior of an aerosol. Particle sizes need to be measured in many situations. For example, particles formed in the semiconductor industry are critical for microcontamination control. Particles formed in chemical reactors are of great interest in material science. To obtain the size information about such particles, differential mobility analyzers are commonly selected as a tool.

Differential mobility analyzers (DMAs) have been widely applied in a variety of aerosol studies and applications, especially for particles in the submicron and nanometer diameter ranges. The DMA method of size classification is based on the electrical mobility of a singly charged particle being inversely related to the size of the particle. A polydisburse aerosol containing singly charged particles over a range of sizes can be classified according to size in an electric field and produces a nearly monodisburse aerosol within a narrow range of electrical mobilities. Thus, the produced aerosol contains particles of substantially the same size. The primary functions of DMAs are for particle sizing and classification. As a sizing instrument, scanning mobility particle analyzers (SMPS) combine a DMA with an ultrafine condensation particle counter (UCPC). For the classification, the evaporation-condensation-DMA classification method has been utilized to generate monodisperse particles. DMAs have also been used to generate PSL standard particles for instrument calibration by removing impurity peak. For bio-application, DMAs with high resolution have been utilized to analyze proteins.

The most widely used DMA is the one commercialized by TSI Inc, St. Paul (TSI Model 3701). Although this DMA works well in the size range of 20 to 500 nm, it becomes increasingly difficult to perform accurate measurement/classification for particles less than 10 nm. The sizing resolution and detection sensitivity of such DMAs deteriorate in the single digit nanometer size range due to Brownian motion of the particles. Meanwhile, nanometer particles have received significant attention because of their special electrical, optical, and/or magnetic properties, making them suitable for high-tech applications. Therefore, it is necessary to develop an optimized DMA able to adequately study aerosols below the 10 nm diameter range.

The diffusion loss inside DMAs increases with smaller particles. The resolution of DMAs worsens with decreasing particles size due to the effect of particle diffusion. To minimize the effect, DMAs with short columns are used to measure particles of single digit nanometer sizes. The largest particle size measured is determined by the maximum electrical strength achievable in a specific DMA. DMAs of long column lengths are needed for larger particles.

Alternative DMAs have been designed for wide particle size ranges. One is an adjustable-column length DMA (ACLDMA) disclosed by Seol et al, 2002 (See Seol, K. S., Yabumoto, J., Takeuchi, K. (2002), "A Differential Mobility Analyzer with Adjustable Column Length for Wide Particle-Size-Range Measurements", J. Aerosol Sci., 33: 1481–1492). By a servomotor and a reducing gear, the classification length of ACLDMA can be adjusted between 0 to 300 mm. ACLDMA can measure a wide particle size range from 1 nm to 500 nm. ACLDMA overcomes the limitation of the traditional DMA of constant classification column. ACLDMA, however, can only classify one particle size at a time as the conventional DMA. For a bi-model distribution aerosol, where the two peaks are far away from each other, ACLDMA cannot measure the two peaks simultaneously. Furthermore, mechanical wear can cause the concern of DMA axial alignment and gas leak. ACLDMA is also much bigger than the conventional DMA Another DMA technique, electric aerosol spectrometer, has also been designed to measure aerosols with wide size range using multi-electrodes. This device has two commercial versions: Differential Mobility Spectrometer (DMS) and TSI 3090 Engine Exhaust Particle Sizer (EEPS), which have been developed to cover the nucleation and accumulation modes in an internal combustion engine exhaust. DMS is able to measure particles in the size range from 5 nm to 1000 nm with 26 electrons. By using electrometer as particle detector, the response time is of 500 ms. Similarly, EEPS is capable of measuring aerosol in the 5.6 nm to 560 nm size range with 22 electrons. The response time of EEPS is 0.1 ms. Both DMS and EEPS are suitable to study transient events in the engine operation.

DMS and EEPS do not have adequate resolution because the entire size range is divided into only 32 channels. Moreover, EEPS can only distinguish two peaks that differ by a factor of 3 in size. Furthermore, there is current leak between the adjacent electrodes, which can interfere with the measurement of particle size distribution. The current leak makes it impossible to measure liquid particles. Therefore, dry air is used to remove any liquid coatings from the solid particles. Due to the detection limit of the electrometer, DMS and EEPS can only measure high concentration aerosol. Since the electrodes are located inside of the classification region, the backgrounds of the electrodes keeping changing with the voltage applied on inner rod. Therefore DMS and EEPS cannot be used to scan particle size distribution in the same way as DMA. Since no sampling flow is drawn out of the instruments, it is impossible to determine their transfer function experimentally. The transfer function is simply obtained by running a model over a range of particle sizes.

SUMMARY

A multi-stage differential mobility analyzer (MDMA) for aerosol measurements includes a first electrode or grid including at least one inlet or injection slit for receiving an aerosol including charged particles for analysis. A second electrode or grid is spaced apart from the first electrode. The second electrode has at least one sampling outlet disposed at a plurality different distances along its length. A volume between the first and the second electrode or grid between the inlet or injection slit and a distal one of the plurality of sampling outlets forms a classifying region, the first and second electrodes for charging to suitable potentials to create an electric field within the classifying region. At least one inlet or injection slit in the second electrode receives a sheath gas flow into an upstream end of the classifying region, wherein each sampling outlet functions as an independent DMA stage and classifies different size ranges of charged particles based on electric mobility simultaneously.

In a preferred embodiment, the first electrode or grid is an inner electrode disposed within the second electrode. Such an arrangement provides an additional particle focusing effect described below. The MDMA can further comprise a flow laminarizor disposed between the inlet or injection slit for receiving the sheath gas flow and the classifying region, wherein the flow laminarizor distributes and laminates the sheath gas flow before entry into the classifying region.

In one embodiment, the MDMA is an axially symmetric (cylindrical) MDMA. In another embodiment, the MDMA is a radially symmetric MDMA.

The independent DMA stages collectively and simultaneously can classify particles sizes from 1 nm (or less) to up to 1000 nm. The MDMA can include a condensation particle counter or induction electrometer connected to each the sampling outlets for counting a number of charged particles. In one embodiment, the MDMA is modularized to allow modification of a number and length of the DMA stages.

A method for measuring a size distribution of aerosols comprises the steps of providing a differential mobility analyzer (MDA), providing an aerosol including a plurality of charged particles for analysis, injecting the aerosol into a classifying region of the MDA bounded by a length between spaced apart and inner and outer electrodes or grids biased at a DC bias voltage to create an electric field therebetween, said outer electrode having at least one sampling outlet disposed at a plurality different distances along the length to provide a plurality of MDA stages each having different classification lengths. A sheath gas flow is injected into an upstream end of the classifying region. The sampling flow is withdrawn using sampling outlets from at least two of the plurality of distances, wherein different particle size peaks are withdrawn from respective sampling outlets. The aerosol is preferably injected from a central inner electrode and the sampling flow is preferably withdrawn through an outer electrode.

In one embodiment, the MDMA is modularized, wherein the method further comprises the step of modifying a number or a length of the DMA stages. The method can further comprise the step of extracting aerosol flow from the MDA at a rate which evenly partitions a flowrate of said aerosol at each of said MDA stages. However, the flow rate for extracting monodisperse aerosol flow from each stage can be varied among the stages, depending on the application. In another embodiment, the extracted aerosol flow rate from the MDA can be equal to the flowrate of the aerosol. The method can further comprising the step of scanning the DC bias voltage. This enables higher resolution sizing measurements.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE PREFERRED EMBODIMENTS

A multi-stage differential mobility analyzer (MDMA) for aerosol measurements includes a first electrode or grid including at least one inlet or injection slit for receiving an aerosol including a plurality of charged particles for analysis. A second electrode or grid is spaced apart from the first electrode. The second electrode has a plurality of spaced apart sampling outlets disposed along its length. A volume between the first and second electrode or grid between the inlet or injection slit and a distal one of the plurality of sampling outlets forms a classifying region, with together with the sampling outlets provide a plurality of essentially independent DMA stages. Being able to perform particle measurement over a wide size range using a single measurement principle eliminates the complexity of previous wide size range particle size measurement systems which rely on two or more measurement principles. For example, the "Wide-Range" particle counter disclosed in U.S. Pat. No. 6,639,671 to Liu requires an optical particle counter for fine particles and a DMA for course particles. In contrast, MDMAs according to the invention allows users to monitor particles over a wide size range with many modes using DMA alone, even when the particle size distribution exhibits a multi-peak or multi-mode shape.

In operation, the first and second electrodes are charged to create a suitable potential difference to create an electric field within the classifying region, wherein the ions are separated in space by combined action of the electric field and a flow of the sheath gas. At least one inlet or injection slit in the first electrode receives a sheath gas flow into an upstream end of the classifying region. Each of the plurality of sampling outlets function as independent DMA stages and can simultaneously classify different size ranges of charged particles based on electric mobility. By scanning a voltage applied to the electrodes, a particle size range can be sampled by each stage.

By providing an MDA having a plurality of different column lengths, MDMAs according to the invention can measure aerosols in a wide size range, such as 1 to 1000 nm, including classifying monodisperse particles of different sizes simultaneously using the plurality of sampling outlets. The length of each stage is designed to cover a subsection of an entire particle size range. The multiple length columns provided by the invention thus allows scanning a smaller range of voltage, thus reducing the scanning time and achieving a fast response, while still covering an entire size range. By preferably having a common base, head and inner rod, the length and number of stages can be varied based on the application, giving the MDMA a high degree of flexibility. The design also allows the operation of high sheath flow for either a high sizing resolution or extending its lower sizing limit to 1 nm or less.

Figure 1A:
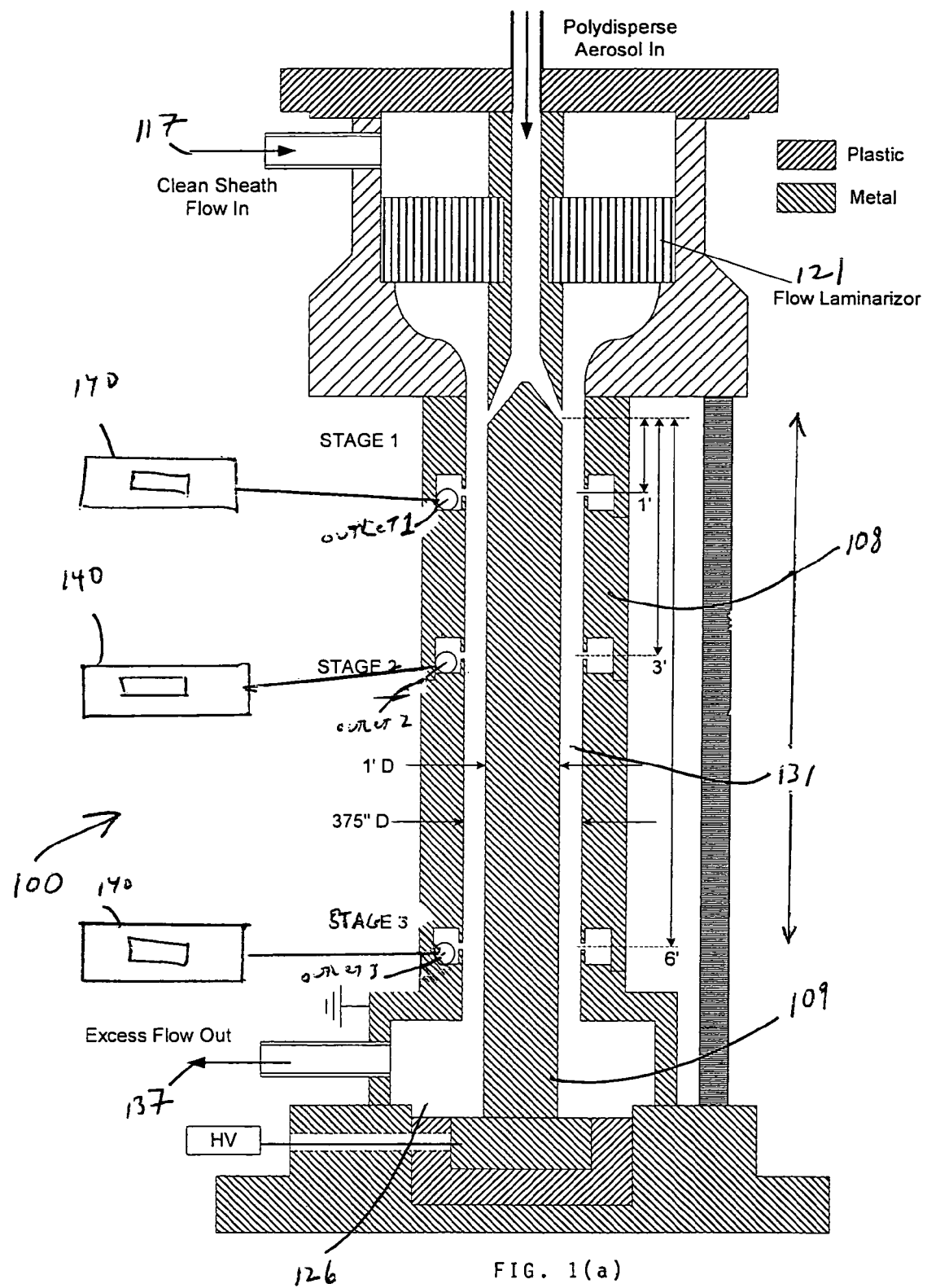
FIG. 1(a) is a schematic diagram of an exemplary cylindrical multi-stage DMA according to an embodiment of the invention.

FIG. 1(a) shows an exemplary cylindrical MDMA 100 having three stages, identified as Stage 1, Stage 2, and Stage 3, which can classify three monodispere particle sizes at the same time. The dimensions shown are arbitrary dimensions. The basic structure of MDMA 100 is axially symmetric and includes ground housing 108 (inner diameter=3.492 cm) and a coaxially aligned inner rod 109 (outer diameter=2.54 cm). The ground housing 108 and inner rod 109 are formed from a metal (or other good electrical conductor) and function as outer and inner electrodes, respectfully. The annular volume between the ground housing 108 and a coaxially aligned inner rod 109 comprise the classifying region 131. The inner rod 109 can be shaped in any form, for instance, rocket shaped. The rod can also be in modular design.

An essentially particle free sheath air enters MDMA through four perpendicular inlets one of which shown as 117, which make it possible to operate the instrument at high sheath flow to achieve better sizing resolution. The sheath flow is then introduced through a flow laminarizor 121. Flow laminarization can be embodied in various arrangements. The invention includes all structures and related methods for keeping the sheath flow laminar. Flow laminarizor 121 is preferably a fine mesh screen, such as a honeycomb metal screen, which evenly distributes and laminates the sheath air before it enters the classifying region 131. Alternatively, a flow contraction arrangement is another option for flow laminarizor 121. The lamination of sheath flow is important to the operation of MDMA 100 since turbulent flow can deteriorate performance.

The inside-out design provided by MDMA 100 is the reverse of the standard DMA arrangement for multi-extraction. In MDMA 100 charged particles are introduced into the center of the annular classifying region 131, surrounded by clean sheath air. The inside-out design provides an unexpected significant advantage. Specifically, the electrical field distortion near the opening of polydisperse aerosol flow passage provides additional particle focusing effect and consequently improves the particle penetration MDMA 100. Based on computer simulations, the electrical field distortion provided by the inside-out design can provide an additional 50% improvement in penetration efficiency. This focusing effect is more pronounced for Stage 1 (shortest length) or when the device is operated at high sheath flowrate.

A charger for charging the aerosol, such as a Kr-85 radioactive neutralizer source, generally provided but is not shown. The aerosol flows axially and divergently downward into the classifying region 131 without mixing with the clean sheath flow. The excess flow is taken out of the classification region 131 through an open chamber 126 to minimize the pressure drop inside MDMA. The bulk excess airflow is then taken out of MDMA through four perpendicular outlets, one of which being shown as 137. Although MDMA 100 is described as having 4 perpendicular inlets 117 and 4 perpendicular outlets 137, a single inlet 117 and outlet 137 will generally be sufficient. The sampling flow is withdrawn from the classifying region 131 at three different locations, such as outlet 1 (2.54 cm), outlet 2 (7.62 cm), and outlet 3 (15.24 cm). The respective outlets are connected to separate condensation particle counters (CPC) or induction electrometers 140 for counting the number of charged particles.

Each stage thus has a different classification length, but shares the same inner electrode 109. In this way, by applying a single voltage on the center rod 109 with respect to ground housing 108, MDMA 100 can classify three monodisperse particle sizes at the same time. Although MDMA 100 includes three stages, the invention is clearly not limited to three stages. The number of stages can be as little as two, or comprises four or more stages. In addition, although shown as being equally spaced from one another, the sampling locations can have variable spacing from one another.

In a preferred embodiment of the invention, the MDMA is a modular design. The size range of particles the MDMA can cover will depend on various operational parameters (flow rate, for example) and the number of stages used. The flexible choice of classifying stages and detector (condensation particle counter or electrometer) make the design modular and user-friendly. The modular design of flexible number of stages enables one to set the desired size range to operate at a much higher scanning rate than the traditional single column DMA and without the limitations of the DMA.

Small particles of high relative electrical mobility are measured at Stage 1 which provides the shortest classification length. This short path can diminish the diffusion broadening effect and diffusion loss of single digit nanometer particles (e.g. 3 nm) and obtain high resolution and detection sensitivity. Large particles with corresponding low electrical mobility are classified by Stage 2 or Stage 3 under the same strength of electrical field. Since sampling flow is withdrawn from MDMA, it is also possible to scan the particle size distribution on each stage by continuously varying the voltage provided by adjustable high voltage applied by high voltage supply 114 on the inner rod 109. MDMA 100 can thus be used to measure particle size distribution over a wide range while keeping the particle classification function.

Figure 1B:
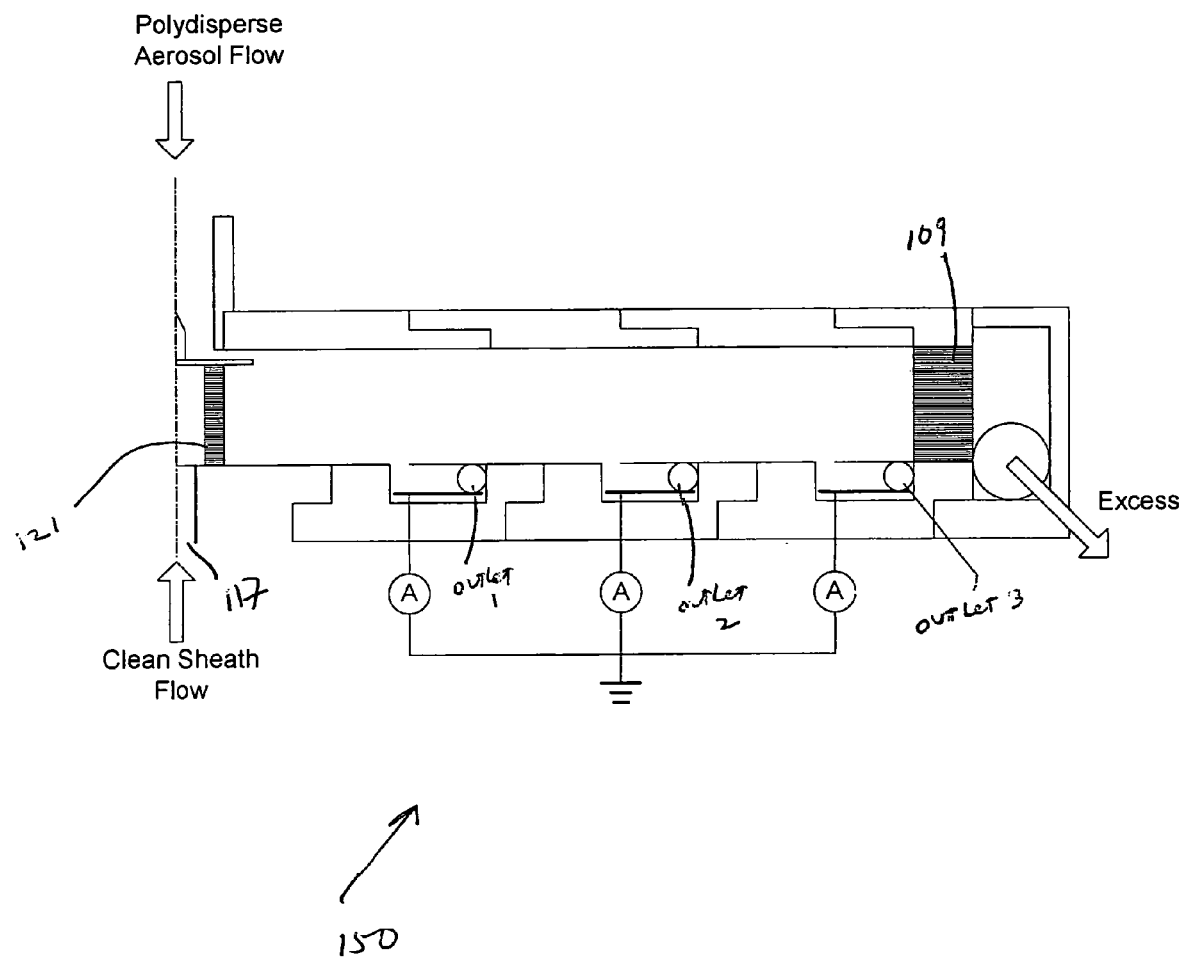
FIG. 1(b) is a schematic diagram of an exemplary radial multi-stage DMA according to an embodiment of the invention.

FIG. 1(b) is a schematic diagram of a radial MDMA 150 according to an embodiment of the invention. A high voltage power supply is not shown. Features analogous to those provided with MDMA 100 are numbered the same. Electrodes can be oriented in various arrangements, depending on the geometry of the electrodes used. For example, electrodes can be placed horizontally. The major differences between MDMA 100 and MDMA 150 are in the supporting structure, the radial design being horizontal thus reducing the need for a high-precision alignment of the stages.

Figure 2:
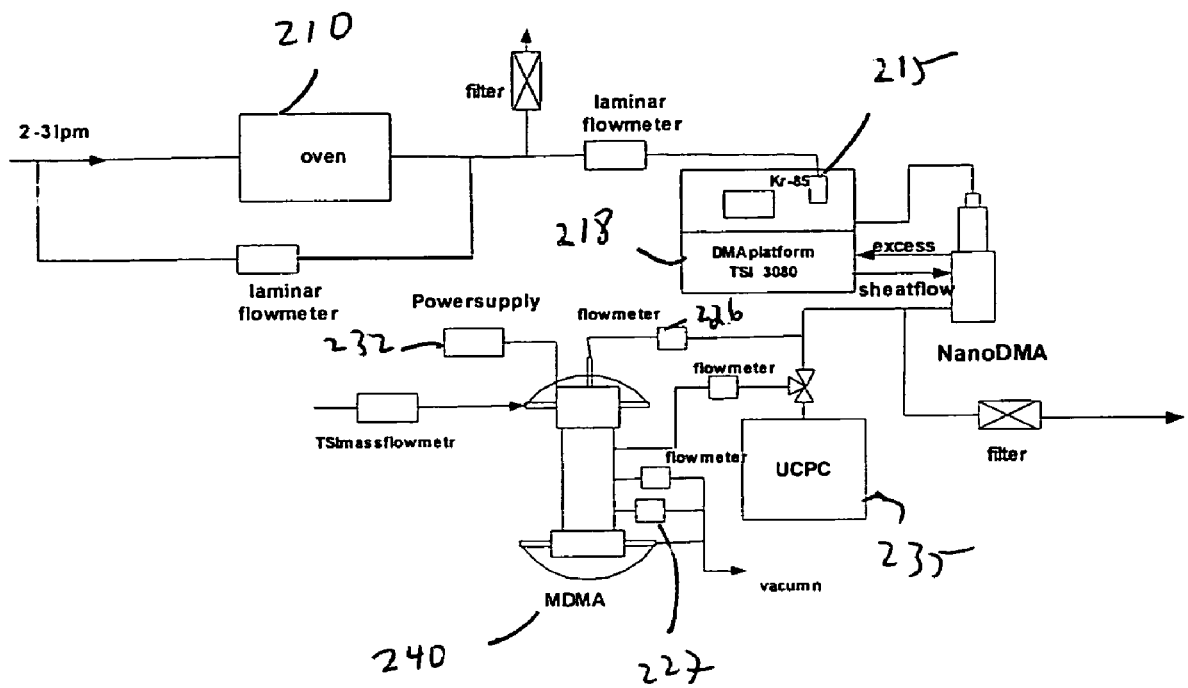
FIG. 2 is a schematic diagram of experimental setup for evaluating the performance of an MDMA.

TDMA Experimental Setup and Deconvolution for MDMA Calibration Experimental Setup It has been demonstrated that transfer function of a DMA can be obtained by operating two identical DMAs in series. Several studies have used this TDMA technique to evaluate the performance of a DMA. FIG. 2 shows an experimental setup for MDMA calibration. Monodisperse silver particles were generated through the evaporation-condensation-DMA classification method. A Lingerberg tube furnace 210 with maximum temperature 1200° C. was used to evaporate silver powder (Aldrich, 99.99%) placed in a combustion boat located in the middle of a ceramic tube ($Al_2O_3$, Coors Ceramics Co). Compressed air at 0.5–1.5 lpm was used as carrier gas to transport the silver vapor out of the furnace. The silver-vapor-rich stream was mixed with a cold stream of air (1.5–2.5 lpm) to quench the hot, silver-vapor-rich stream at the exit of the ceramic tube. Polydisperse silver particles in the nanometer size range were then generated through nucleation and condensation. By varying the furnace temperature and the quenching flowrate, the mean size and concentration of polydisperse silver particles was thus controlled.

To obtain monodisperse silver particles of the desired sizes, the polydisperse particle stream was passed through a Kr-85 radioactive neutralizer 215 and a Nano-DMA (TSI Model 3085) 218. A laminar flowmeter 226 was used to monitor the flowrate of the polydisperse aerosol stream. The sheath flow and voltage of Nano-DMA were controlled by a DMA platform (TSI Model 3080). A constant voltage was applied to Nano-DMA to generate monodisperse particles. Monodisperse particles were then sent into MDMA 240 to study its performance. In order to achieve high aerosol flow operation, a T-connector was used to add extra clean and dry air to the aerosol stream. Three laminar flowmeters 227 was employed to control the aerosol flows extracted from MDMA. Two TSI mass flowmeters (model 4000) were used to indicate the sheath and excess flow. A Bertan high voltage supply (206B-10R) 232 was used to apply voltage onto the inner rod. An ultrafine condensation particle counter (UCPC; TSI Model 3025A) 235 was used as particle detector. A three-way valve was used in order to measure the particle concentrations at the inlet and outlet of MDMA. Since there are not two identical MDMAs available, a NanoDMA (Chen, D., David Y. H. Pui, D. Hummes, H. Fissan, F. R. Quant and G. J. Sem, (1998) "Design and Evaluation of a Nanometer Aerosol Differential Mobility Analyzer (Nano-DMA)", J. Aerosol Sci., for the Special Issue on Nanometer Particles, 29, 497–509; hereafter Chen et al.) was utilized as the first DMA to generate monodisperse particles. For the NanoDMA, two flow conditions, 1.5/15 and 0.75/15 (lpm/lpm) for aerosol/sheath flow rates, were used to keep the input mobility distributions of about the same width as the MDMA transfer function.

The voltage applied on the first DMA 218 was then fixed for the desired particle size. The voltage on the second DMA 240 is varied. With a particle counter UCPC 235, the particle concentration at the exit of second DMA 240 is recorded as the function of scanned voltage. With the measured particle concentration at the exit of first DMA 218, the TDMA curve is then obtained by normalizing the recorded concentration at the outlet of second DMA 240 with the concentration at the exit of first DMA 218. Seven particle sizes were evaluated, namely, 6, 8, 10, 14, 20, 30 and 45 nm.

The simultaneous classification of monodisperse particles will facilitate the development of a variety of nanoparticle applications, including industrial applications. The invention can be used for obtaining size distributions of aerosols in, for example, fundamental research, inhalation toxicology, pharmaceutical, powder manufacturing, homeland security for detection of explosives debris, incidental release of particles from energetic materials, virus detection, combustion emissions, environmental monitoring, and space exploration.

The miniaturization of devices according to the invention is very straightforward. The invention can be embodied as a portable apparatus in a box of the size of 2' H×2' W×2' D, for example, and weigh around 60 lbs or less. There is no specific requirement for power for the device, other than DC high voltage.

EXAMPLES

The present invention is further illustrated by the following specific Examples, which should not be construed as limiting the scope or content of the invention in any way.

Calibration of Central Electrode Voltage

Theoretical central voltage (Vt) was calculated by equation (1) based on Knutson and Whitby:

$$V_t = \frac{(q_c + q_m)\ln(R_2/R_1)}{4\pi L Z_p^*} \quad (1)$$

where $q_c$ is the sheath flow rate, $q_m$ is the excess flow rate, $R_1$ is the outer radius of the center rod (1.27 cm), $R_2$ is the inner radius of the MDMA (1.746 cm), L is the classification length for each stage, and $Z_p^*$ is the central mobility of first DMA. Since sampling flow is extracted from each stage in MDMAs 100 and 150, the flowrate ratio of polydisperse aerosol and sheath flows are different for each of the three stages. A method is described herein calculate the sheath flow at each stage. The sheath flow at first stage is the clean air introduced into MDMA. The sheath flow subtracting sampling flow at the first stage is equal to the sheath flow at second stage. This sheath flow plus the aerosol flow is the excess flow at the second stage. The same principle applies to the third stage.

Central voltage is important for DMA sizing and classification. Using the same setup shown in FIG. 2, the theoretical and calculated central voltages were compared under two different operation conditions. One method is to extract aerosol flow with the rate equal to evenly partition the polydisperse aerosol flowrate at each stage, and the other is to extract aerosol flow with the rate the same as polydisperse aerosol flowrates. The sheath and aerosol flows were fixed at 20 and 2.4 lpm. The sampling flow at each stage was 0.8 lpm and 2.4 lpm under these two sampling flow operation schemes. Experimental central voltage is the voltage corresponding to the highest concentration detected at the exit of MDMA.

Figure 3A:
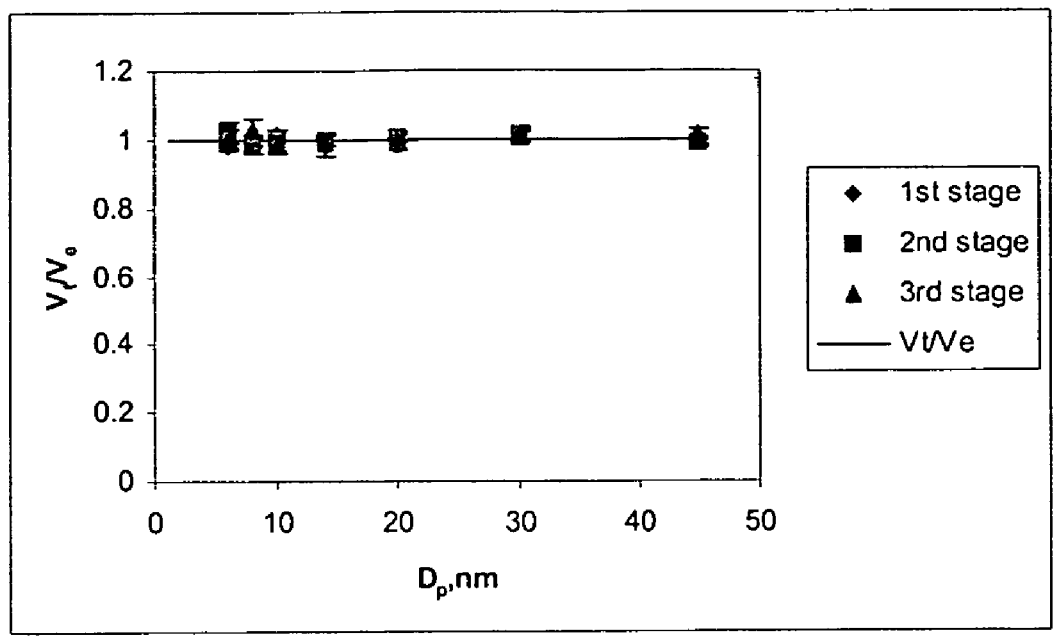
FIG. 3 shows a comparison of theoretical central voltage, $V_t$, and measured central voltage, $V_e$, under different operation conditions: (a) sampling flow rate 2.4 lpm; (b) sampling flow rate 0.8 lpm. The sheath and aerosol flow rate were kept 20 and 2.4 lpm, respectively.
Figure 3B:
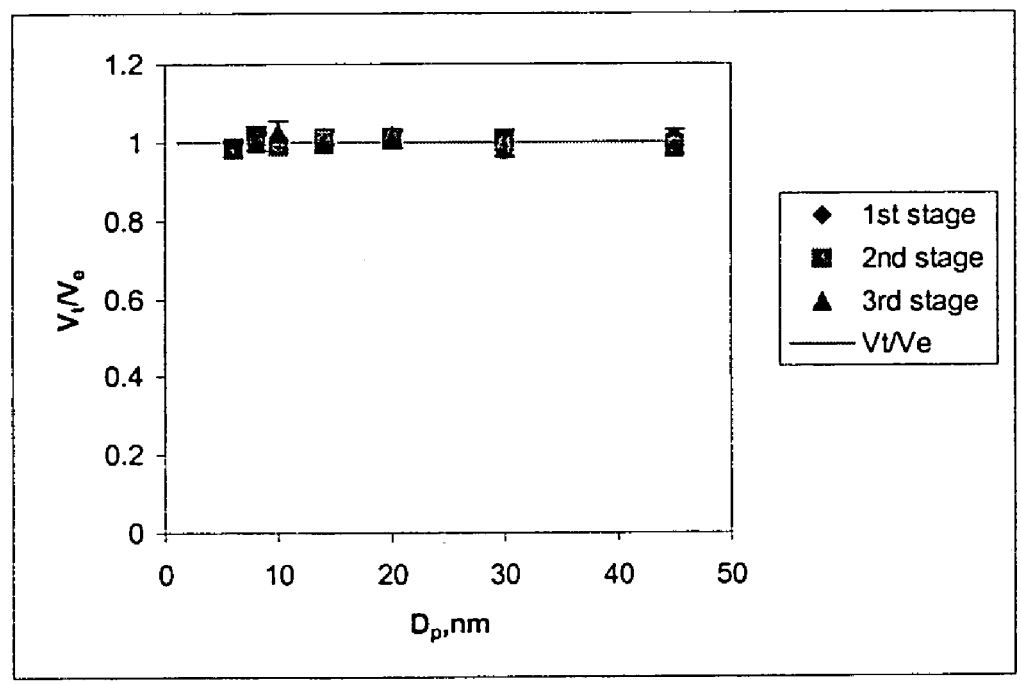

FIGS. 3(a) and 3(b) show the ratios of theoretical central voltage (Vt) to experimental central voltage (Ve) are very closed to 1 for both cases. There is good agreement between the experimental and the theoretical central voltage at all stages under different operational conditions. Under second operational scheme, even though more than 10% of sheath flow was withdrawn from each stage, the central voltage can still be predicted accurately. Due to the extraction of sampling flow, the sheath flow at third stage is less than those in the first and second stages. Lower voltage is needed to measure large particles at third stage, which extending the upper detection limit and covers wider aerosol measuring size range. Since a UCPC was used as particle detector, it has about a five percent fluctuation in concentration detection. The deviation is within the experimental error.

MDMA Transfer Function

Figure 4A:
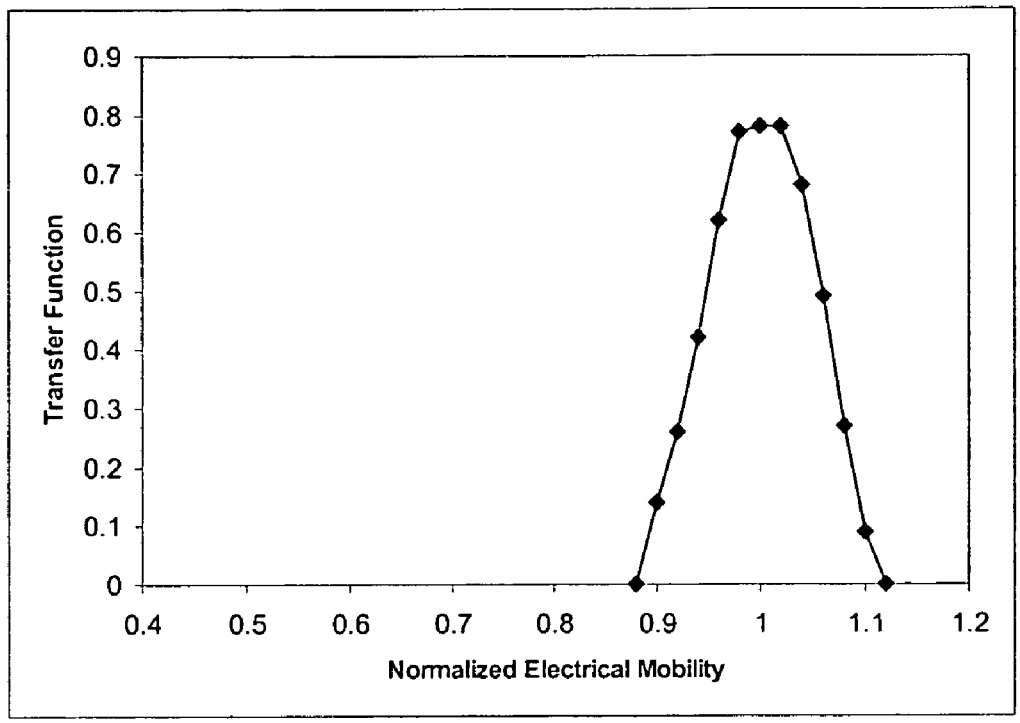
FIG. 4(a) shows the transfer function of a MDMA obtained using linear-piecewise deconvolution scheme at the third stage; (b) Comparison of experimental and numerical TDMA curve. The sheath, aerosol, and sampling flowrates were kept at 20, 2.4, and 0.8 lpm, respectively. The particle size selected was 20 nm.
Figure 4B:
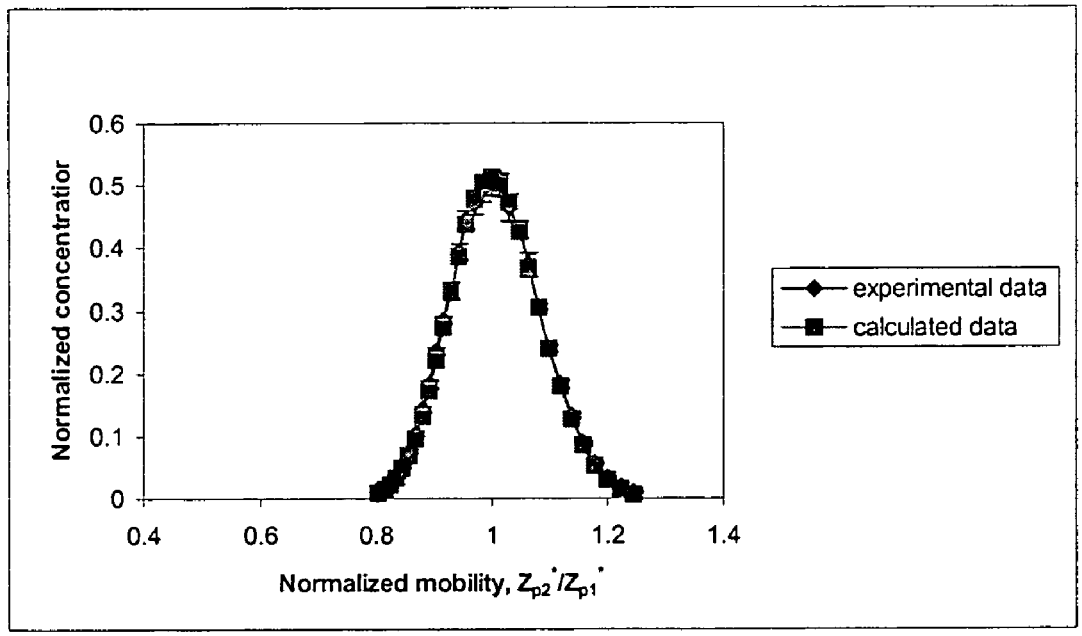

FIG. 4(a) shows the transfer function of 20 nm particles obtained using linear-piecewise-function scheme at the third stage for 20 lpm sheath flow rate, 2.4 lpm aerosol flow rate, and 0.8 lpm sampling flow rate. As expected, the shape of the transfer function is trapezoidal given that the aerosol flow is not equal to the sampling flow. The half-width is approximate 0.125, which is the same as theoretical value calculated by equation (2):

$$\text{Half-width} = \beta^*(1+|\delta|) \quad (2)$$

where $\beta=(q_s+q_a)/(q_m+q_c)$, $\delta=(q_s-q_a)/(q_s+q_a)$, $q_c$ is the sheath flow rate, $q_m$ is the excess flow rate, $q_s$ is the sampling flow rate, $q_a$ is the aerosol flow rate. FIG. 4(b) illustrates that the calculated TDMA curve agrees well with the experimental one. Every data point is within the experimental error.

Resolution

Since MDMA 100 and 150 have three stages, there are many operation combinations between aerosol and sampling flows. Two basic cases were tested in this study: sampling flow equal to evenly partition the polydisperse aerosol flowrate at each stage and sampling flow with the rate the same as polydisperse aerosol flowrate.

Figure 5A:
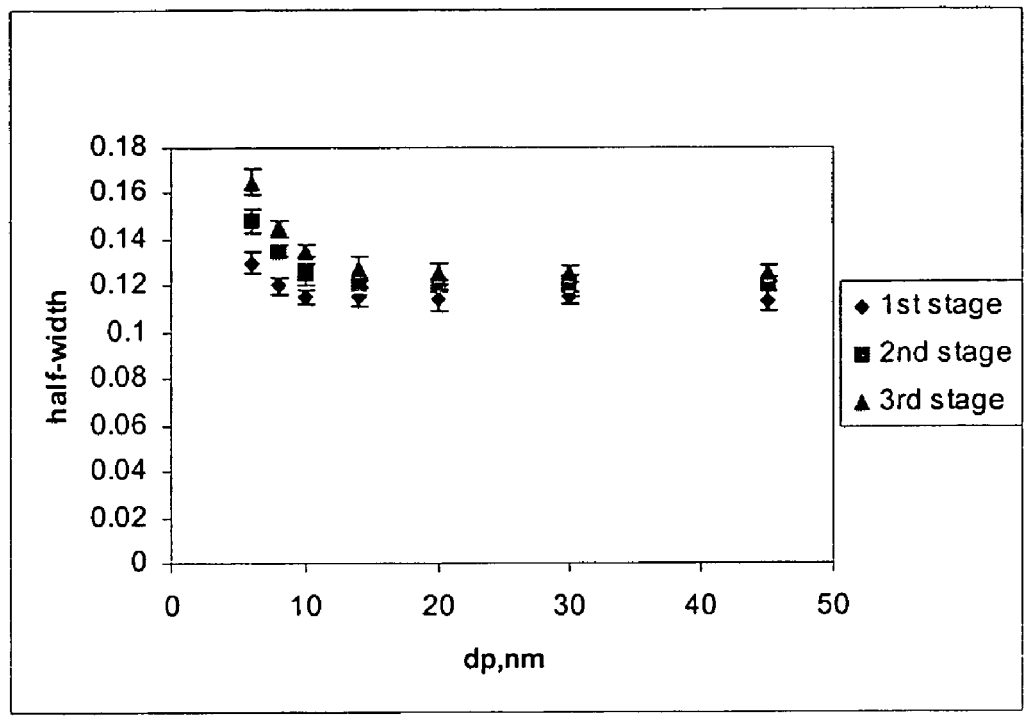
FIG. 5 shows the half-width of the deconvoluted true transfer function of MDMA: (a) at 2.4 lpm/0.8 lpm/20 lpm aerosol/sampling/sheath flow rates; (b) at 2.4 lpm/2.4 lpm/20 lpm aerosol/sampling/sheath flow rates.

FIG. 5(a) shows the half-width of the deconvoluted true transfer function of MDMA at sheath flow 20 lpm, aerosol flow 2.4 lpm, 0.8 lpm sampling flow each stage as a function of particle sizes at three stages. The half-width is a measure of the sizing resolution of the MDMA. Due to particle Brownian diffusion, the half-width is increased with decreasing particle size. Three stages follow the same trend. The first stage has the shortest classification length. As a result of decreasing resident time, it has the smallest half-width. The first stage gives the best performance. Due to the aerosol sampling, the sheath flow and excess flow at each stage is different. The theoretical half-width, therefore, is also slightly different. The first stage has the highest sheath flow and narrowest transfer function. Based on the condition used, the theoretical half-widths are 0.115, 0.12, 0.125 for each stage. It is seen that the resolution of the MDMA is nearly idea down to 10 nm at first stage, 14 nm at second stage and 20 nm at third stage before it begins to level off the ideal condition.

Figure 5B:
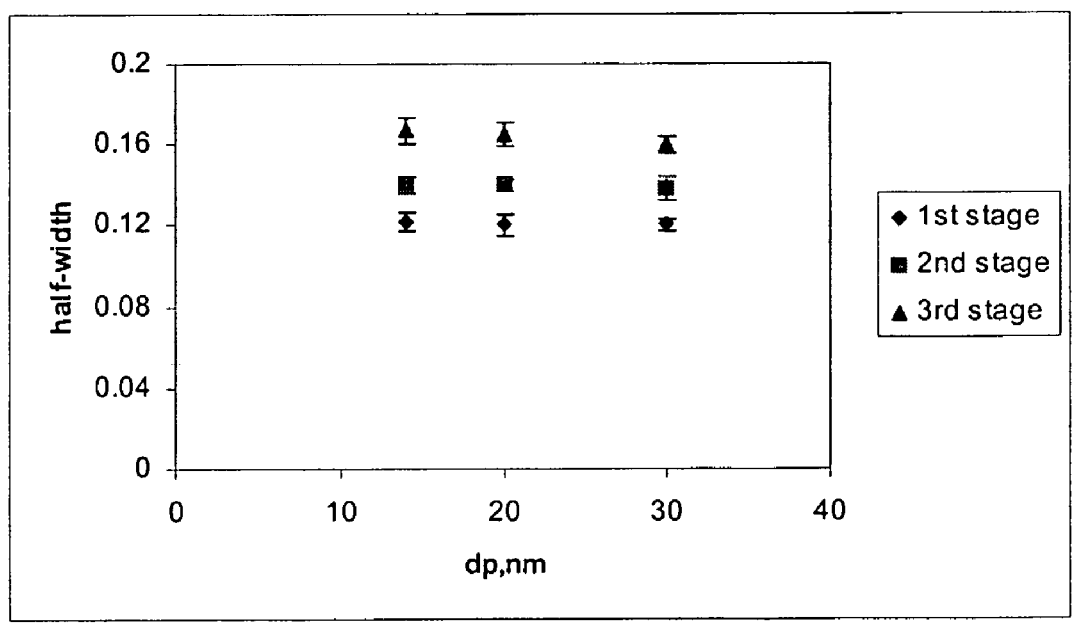

FIG. 5(b) demonstrates the half-width MDMA at sheath flow 20 lpm, aerosol flow 2.4 lpm, 2.4 lpm sampling flow at each stage for large particle sizes. Since more than 10% of sheath flow was taken out, the resolution of MDMA increases noticeably as a result of decreasing sheath flow. Having 20 lpm sheath flow at first stage, 17.6 lpm at second stage, and 15.2 lpm at third stage, the theoretical half-widths are 0.12, 0.136, and 0.158. As shown in FIG. 5(b), the half-width at three stages are very close to the theoretical predictions. Relatively large amount of sheath flow extraction does not deteriorate the performance of MDMA. The resolution of the instrument is still predictable. At first stage, these two different operations give comparable resolution.

Figure 6:
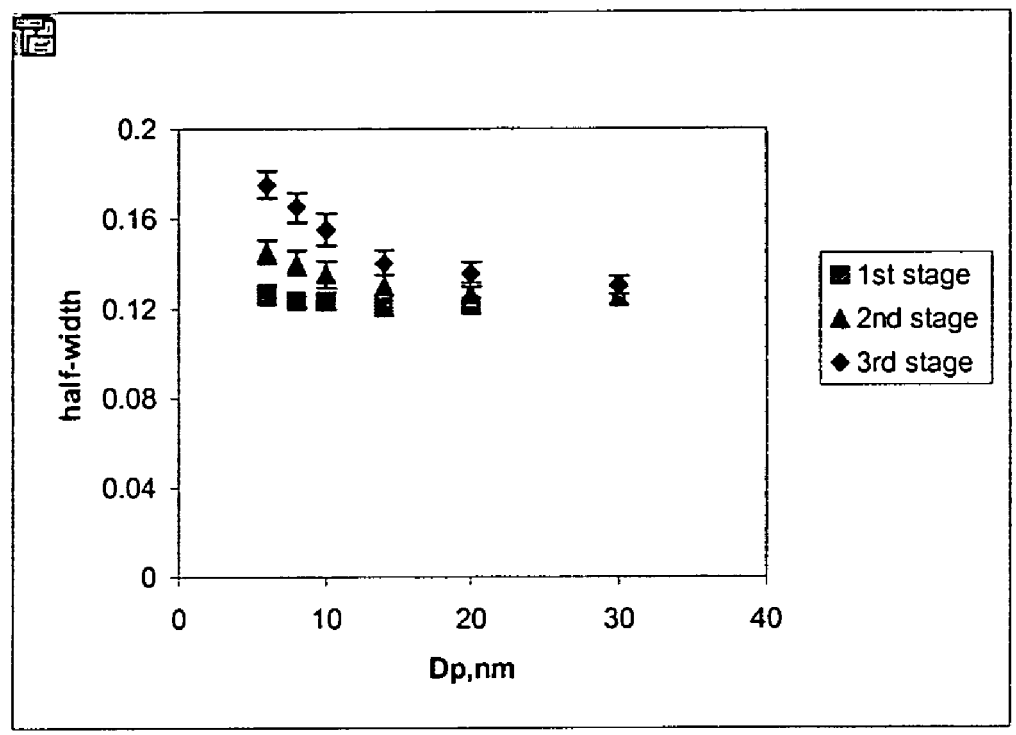
FIG. 6 shows the half-width of the deconvoluted true transfer function of MDMA: (a) at 4.5 lpm/1.5 lpm/36 lpm aerosol/sampling/sheath flow rates; (b) at 1.5 lpm/1.5 lpm/36 lpm aerosol/sampling/sheath flow rates.
Figure 6:
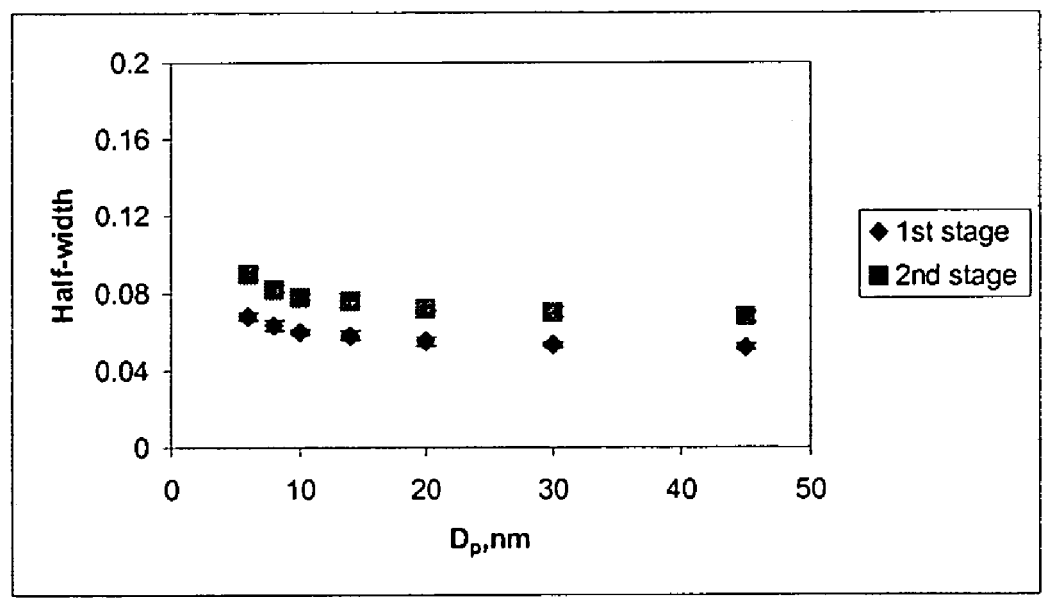

The performance of MDMA was also evaluated at higher sheath flow 36 lpm under two different operation schemes described above. In this test, the sampling flow at each stage was fixed at 1.5 lpm. In one case the aerosol flow was equal to the sum of sampling flows 4.5 lpm. Under ideal situation, the half-width of transfer function should have values of 0.12, 0.125, 0.13 at first, second and third stages. As shown in FIG. 6(a), the sizing resolution all approaches the theoretical value for large particles at three stages. The half-width increases as the particle size decreases because of particle Brownian diffusion. Due to the shortest length at the first stage, the half-width increases slightly even for 6 nm particles. FIG. 6(b) shows the half-width of MDMA for the case when aerosol flow is equal to sampling flow 1.5 lpm at first two stages. The theoretical half-width is 0.0417, 0.0436 at respective stages. Compared with FIG. 6(a), the resolution of MDMA is improved with smaller aerosol/sheath flow ratio. Deviations have been observed between the numerical and experimental data. This is probably due to two reasons: (1) The experimental error resulting form flow rates and concentration measurement have a bigger effect on deconvoluted transfer function when the windows of TDMA curves are relatively narrow. (2) Flow mismatch is likely to happen in the aerosol and sheath flow at the entrance slit to the classification area due to the fairly big velocity difference between the aerosol and sheath flows. The flow disturbance can cause the broadening of the transfer function.

From the discussion above, different operational conditions give this device maximum flexibility. Fixing the sheath flow rate, if the sizing resolution is a concern, small aerosol/sheath flow ratio is a desired operation scheme. If the diffusion loss in the transport passage becomes a concern, higher aerosol flow can be used.

Figure 7:
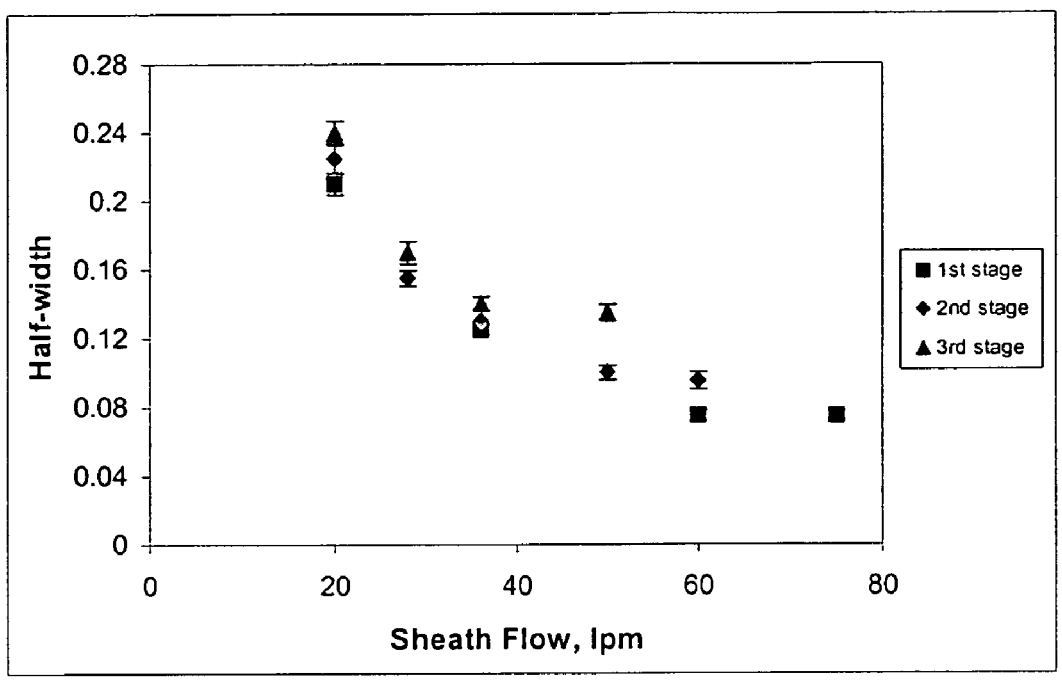
FIG. 7 shows the sheath flow effect on MDMA sizing resolution at aerosol flow 4.5 lpm and the sampling flow 1.5 lpm at each stage. The particle size selected was 20 nm.

The limits of the sheath flow at three stages were tested. As is known, the sizing resolution is a function of flow rates. If the aerosol flow and sampling flow were fixed, half-width will reduces and better resolution will achieve as sheath flow increases. FIG. 7 shows the sheath flow effect. The aerosol flow was fixed at 4.5 lpm and the sampling flow at each stage was 1.5 lpm. The particle size selected was 20 nm. As shown in the graph, half-width decreases with increasing sheath flow rate, as predicted by the theory. Better measurement and classification is achieved at high sheath flow rate when the aerosol flow and sampling flow are fixed. The sheath flow can go up to 75 lpm at first stage, 60 lpm at second stage, and 50 lpm at third stage. Operated at higher sheath flows, the half-width deviated from the theoretical trend. It is probably because flow disturbance in the classification region is likely to happen at high Reynolds number. Due to the longer classification length of the second and third stages, the effect of flow disturbance is more obvious at a lower Reynolds number.

Figure 8:
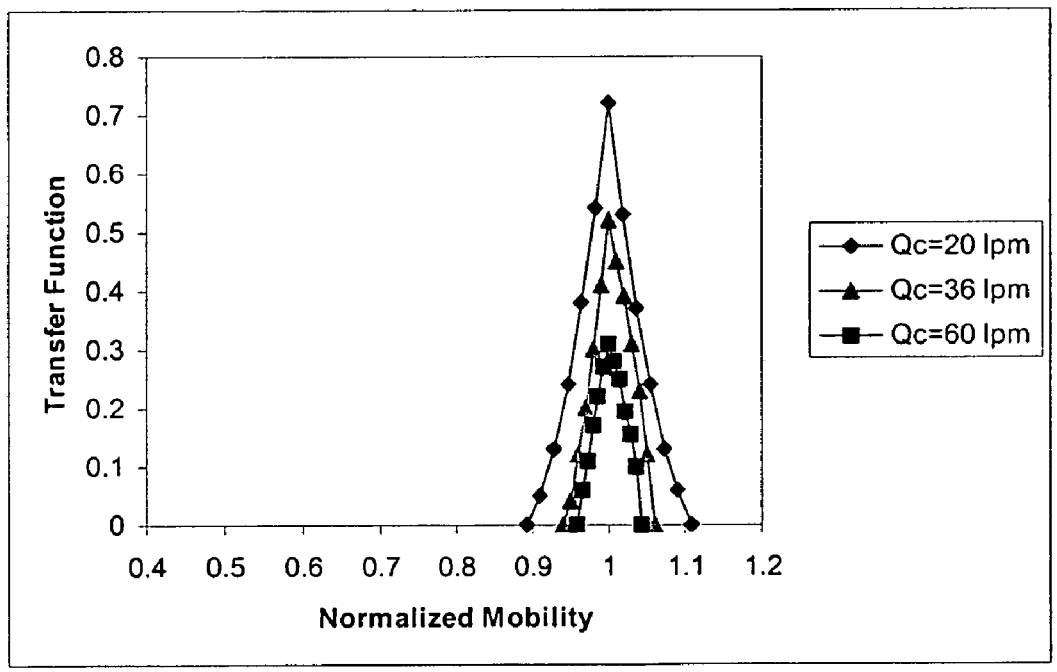
FIG. 8 shows the true transfer function of MDMA at different sheath flow rates 20, 36 and 60 lpm at the first stage. The aerosol and sampling flow rate were kept 1.5 lpm. The particle size selected was 20 nm.

The true transfer function of MDMA at different sheath flow rates are illustrated in FIG. 8 for 20 nm particle at first stage. There are the cases for 1.5/1.5/20, 1.5/1.5/36, and 1.5/1.5/60 (aerosol/sampling/sheath) flow rates. As expected, the shape of the transfer function is triangular since the aerosol flow is equal to the sampling flow. Under ideal situation, the half-width of the transfer function should be 0.075, 0.042, and 0.025 for individual flow rates. The half-width has values of 0.075, 0.06, and 0.04 from experimental calibration. To obtain accurate size distribution, it is important to operate the classifier at a high ratio of sheath to aerosol flow rate. There is good agreement between experimental and theoretical data at 1.5/1.5/20 (aerosol/sampling/sheath) flow ratio. For other two cases, some differences are observed. One possible explanation is that the transfer function is relatively narrow at low aerosol-to-sheath flow ratios. The deconvolution half-width is easily influenced by the experimental errors. This effect becomes more severe at lower aerosol-to-sheath flow ratio. As shown in the graph, operated at high sheath flow rate, MDMA can achieve high resolution while maintain reasonably high aerosol and sampling flow rates to reduce losses in the transportation passage.

Sensitivity

Figure 9:
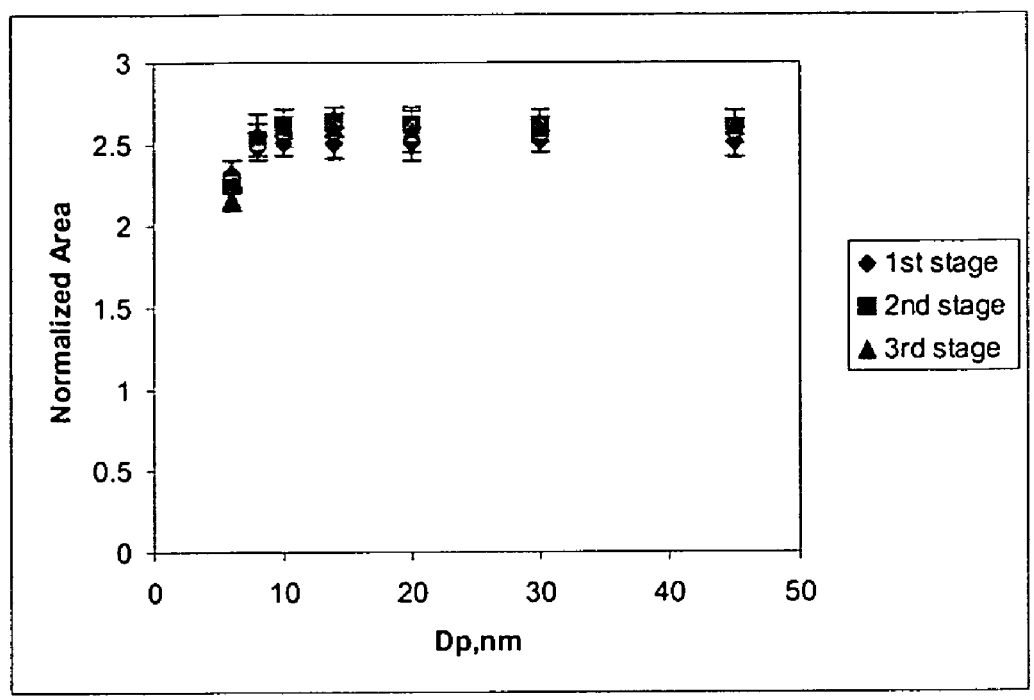
FIG. 9 shows the normalized area of MDMA transfer function: (a) at sheath flow rate 20 lpm, aerosol flow rate 2.4 lpm and 0.8 lpm sampling flow rate; (b) at sheath flow rate 20 lpm, aerosol flow rate 2.4 lpm and 2.4 lpm sampling flow rate.
Figure 9:
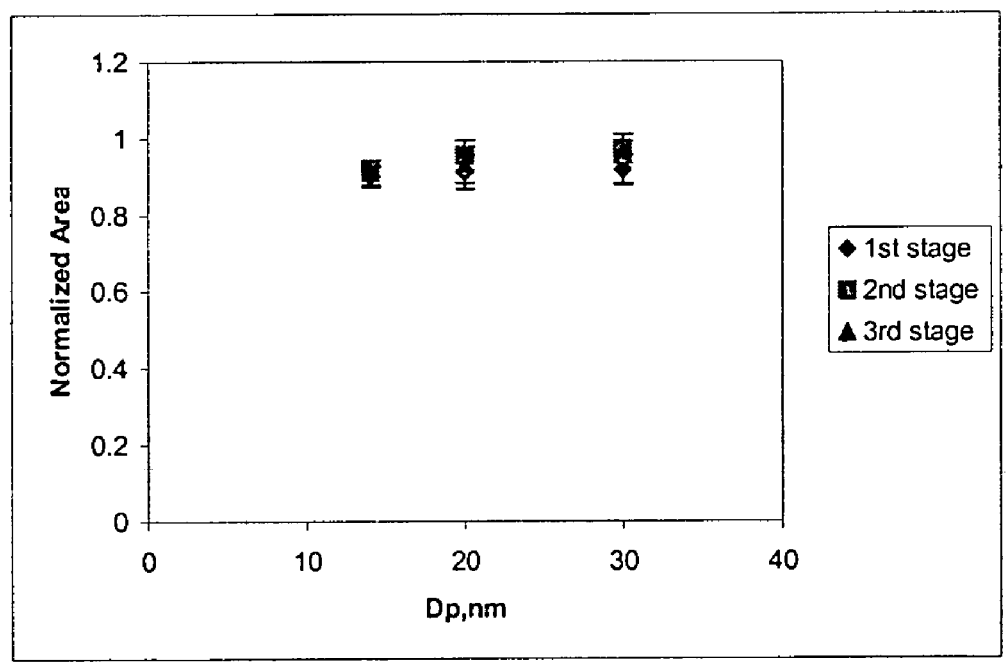

Another important performance parameter is diffusion loss in a DMA. Accounting for diffusion broadening but not diffusion loss, the transfer function becomes shorter and wider while maintaining the same area. Considering both effects, the area of transfer function is smaller than those of the above two functions. Thus the area of transfer function gives a measure of the transmission efficiency of DMA. FIG. 9(a) shows the normalized area of transfer function as a function of particle size at sheath flow 20 lpm, aerosol flow 2.4 lpm and 0.8 lpm sampling flow at each stage. Under ideal condition, the transfer function has a shape of trapezoid stage given that the aerosol flow is not equal to sampling flow. Due to aerosol flow sampling, the area of transfer function has a slightly different value at each stage, 0.038, 0.0396, and 0.0415. As shown in the graph, the normalized area is nearly a constant down to 8 nm before it begins to decrease. Slight Diffusion loss is observed for 6 nm particles. Even though the half-width increases with increasing classification length as shown in FIG. 5(a), the normalized area is almost the same at three stages for a specific particle size. It demonstrates that the diffusion loss in the classification region is relatively small. The increment in half-width is due to diffusion broadening effect. The ratio of the measured area to the theoretical one is much larger than 1. This is probably because some assumptions made in the theoretical derivation may not be valid in the real operation. Due to relatively wide entrance slit designed for high aerosol flow operation, the electrical field penetration problem is not negligible. In addition, high voltage is applied on the upper and lower parts of the entrance slit. The electrical field points to the center of the entrance slit, where the potential is low. This configuration tends to focus the aerosol to the center of the aerosol stream. When aerosol flow is not equal to sampling low, only central aerosol flow is extracted from MDMA. The focusing effect may actually increase the penetration of particles through MDMA, which causes the area of real transfer function larger than the theoretical one. Furthermore, due to the electrical distortion, the assumption that no variation in aerosol concentration across the inlet is not valid any more. The inlet aerosol concentration could be parabolic or other distribution function. The effect was expected to be more severe under high sheath flow operation when higher voltage is needed to classify certain size particles.

FIG. 9(b) shows the normalized area of MDMA transfer function for the case of extracting sampling flow with the rate the same as polydisperse aerosol flowrate, i.e. sheath flow 20 lpm, aerosol flow 2.4 lpm, and sampling flow 2.4 lpm at each stage. For the present condition of equal aerosol inlet flow and sampled outlet flow, the ideal transfer function would be a triangle function with a height of 1.0 and half-widths of 0.12, 0.136, 0.158, resulting in areas of 0.12, 0.136, 0.158 at each stage. All curves almost reach 1 for large particles indicating neglectable transport losses for such particles. Again, no loss was observed in the classification region for particles larger than 10 nm. The normalized area is almost the same for three stages. Since aerosol flow is the same as sampling flow, the aerosol focusing effect in the entrance slit caused by the electrical field penetration is nearly eliminated compared with that encountered in FIG. 9(a).

Figure 10A:
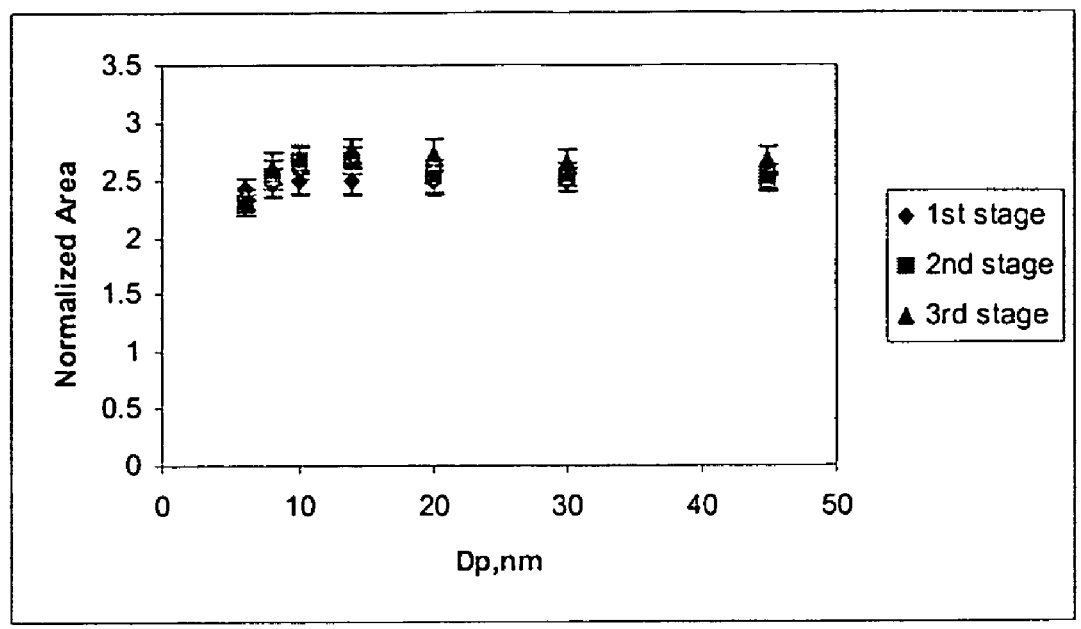
FIG. 10 shows the normalized area of MDMA transfer function: (a) at sheath flow rate 36 lpm, aerosol flow rate 4.5 lpm and 1.5 lpm sampling flow rate; (b) at sheath flow rate 36 lpm, aerosol flow rate 1.5 lpm and 1.5 lpm sampling flow rate.

The normalized area of MDMA transfer function is plotted as a function of particle diameter in FIG. 10(a) for the case of sheath flow 36 lpm, aerosol inlet flow 4.5 lpm and sampled outlet flow 1.5 lpm at each stage. The ideal transfer function would have an area of 0.0396, 0.04125, and 0.0429 at each stage. A same phenomenon is observed as in FIG. 9(a). The normalized area is much larger than 1 at three stages for the entire particle size. A possible explanation has been discussed above. Having nearly the same flow ratio as that in FIG. 9(a), high aerosol and sheath flows, as expected, gives higher normalized area (higher detection sensitivity) for 6 nm particles. The high flow feather reduces the resident time in MDMA, which diminishes diffusion loss of the nanometer particles in the transport path. Not much difference is observed for large particles under these two flow operations.

Figure 10B:
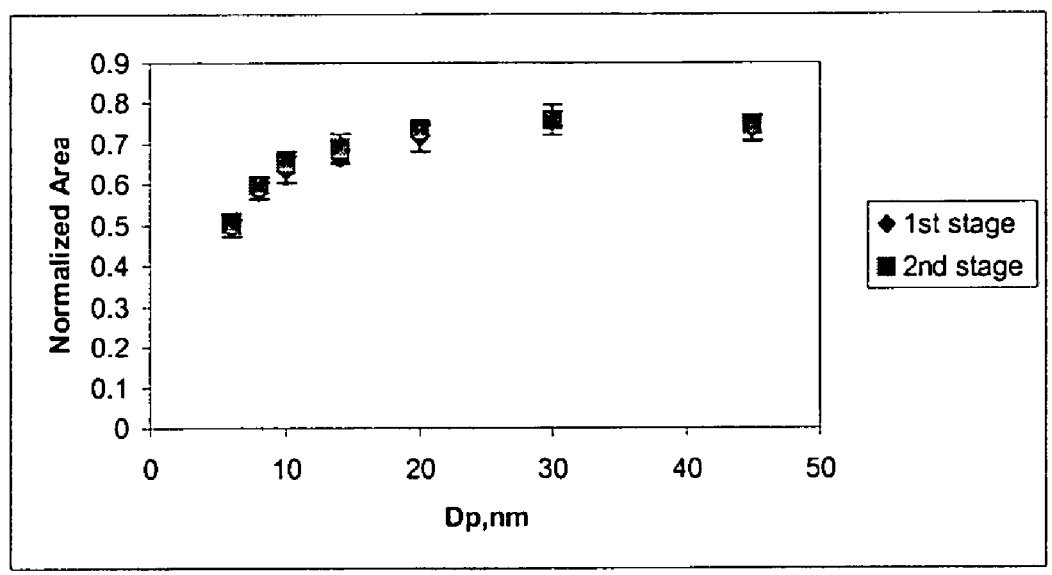

FIG. 10 also includes the normalized area of deconvoluted transfer function for the case of sheath flow 36 lpm and equal aerosol and sampling flow 1.5 lpm, as a function of particle size. Operated under same aerosol and sampling flow, the ideal areas of transfer function are 0.042 and 0.0435 at first two stages. Due to Brownian diffusion, the normalized area of transfer function is reduced as the particle size decreases. The normalized area remains the same for certain size particles at different stages, indicating no significant loss in the classification region. The loss is probably due to a mismatch in the aerosol and sheath flow at the entrance slit to the classification area, which happens at high sheath/aerosol flow. The aerosol flow is pushed to a narrow area near the inner wall and diffusion loss is likely to occur easily. Diffusion has a greater impact on the higher ratio of sheath to aerosol flow. Even for large particle size, the normalized area is smaller than that in FIG. 9(b).

MDMA Transfer Function at High Flow Operation

Figure 11:
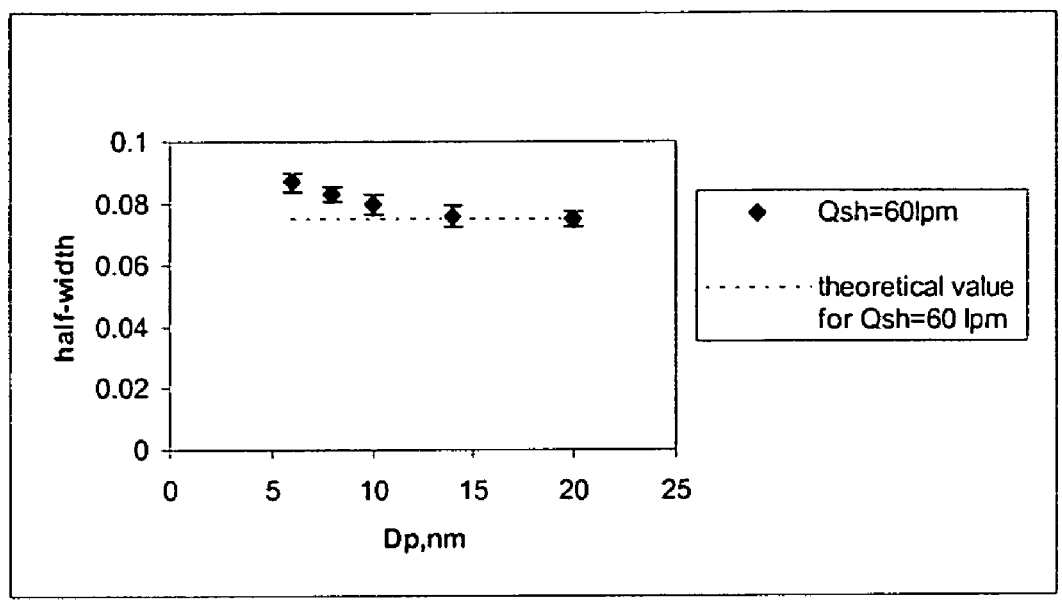
FIG. 11 shows the MDMA transfer function: (a) the half-width and (b) the normalized area at the first stage for sheath flow rate 60 lpm, aerosol flow rate 4.5 lpm, and sampling flow rate 1.5 lpm at each stage.
Figure 11:
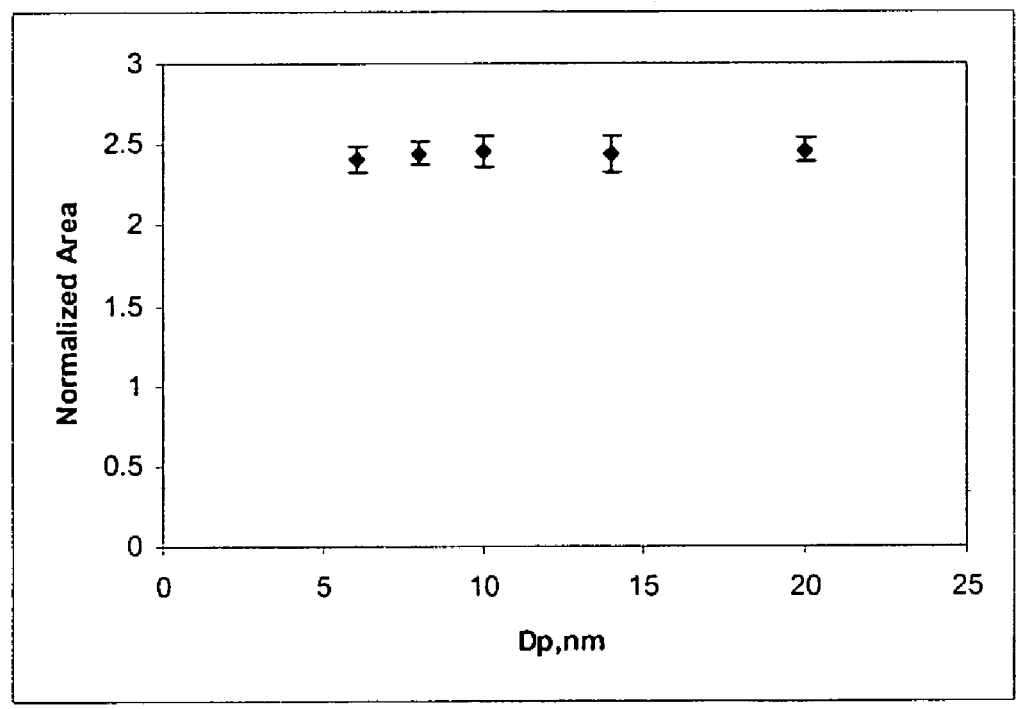

FIG. 11 shows (a) the half-width and (b) the normalized area of the deconvoluted transfer function of MDMA under high flow operation at the first stage for sheath flow 60 lpm, aerosol flow 4.5 lpm, and sampling flow 1.5 lpm at each stage. The half-width approaches a constant value as the particle size increases. This value is nearly equal to the value of 0.073, which is predicted theoretically for the selected flow settings. By using high aerosol flow rate 4.5 lpm and sheath flow rate 60 lpm, the diffusion broadening affect is reduced. The half-width deviates slightly from the theoretical value even for 6 nm particle. The diffusion loss in the aerosol transport passages is also significantly reduced. The normalized area decreases slightly for particles less than 10 nm as a result of decreasing resident time. This is a huge advantage of MDMA. It can be operated at high sheath and aerosol flow to diminish the diffusion loss and broadening effect. For current TSI 3071 and NanoDMA, the sheath flow can only go up to 15 lpm. Low aerosol flow has to be used in order to obtain high sizing resolution. However, the diffusion loss and broadening effect become an issue for particles less than 10 nm.

Figure 12:
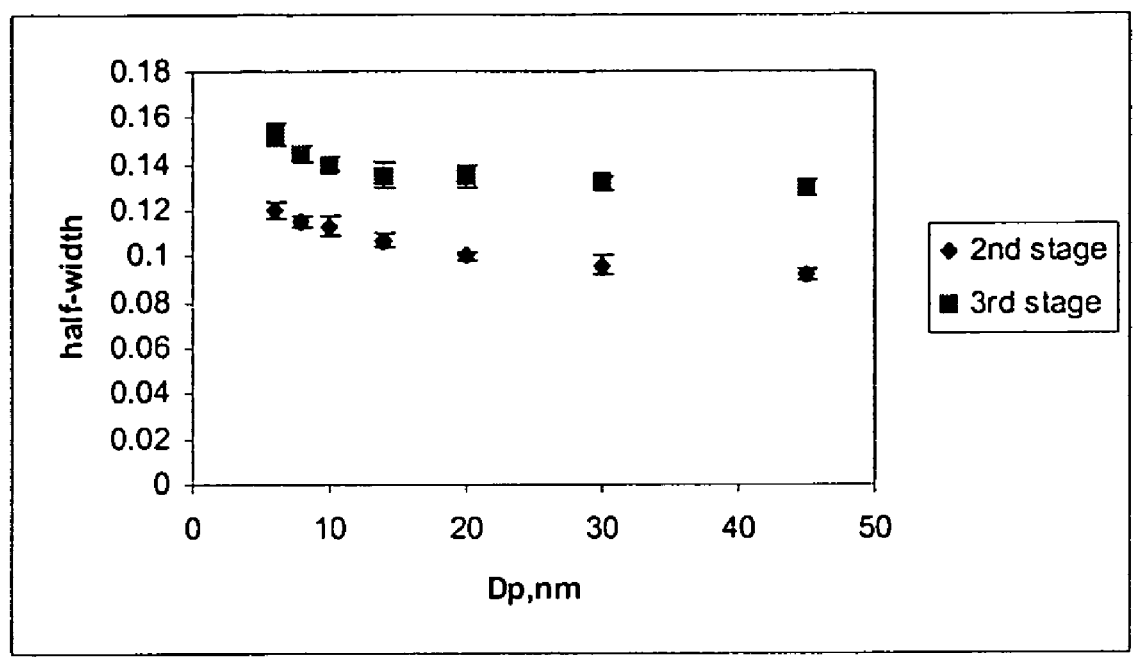
FIG. 12 shows the MDMA transfer function: (a) the half-width and (b) the normalized area at the second and third stage for sheath flow rate 50 lpm, aerosol flow rate 4.5 lpm, and sampling flow rate 1.5 lpm at each stage.
Figure 12:
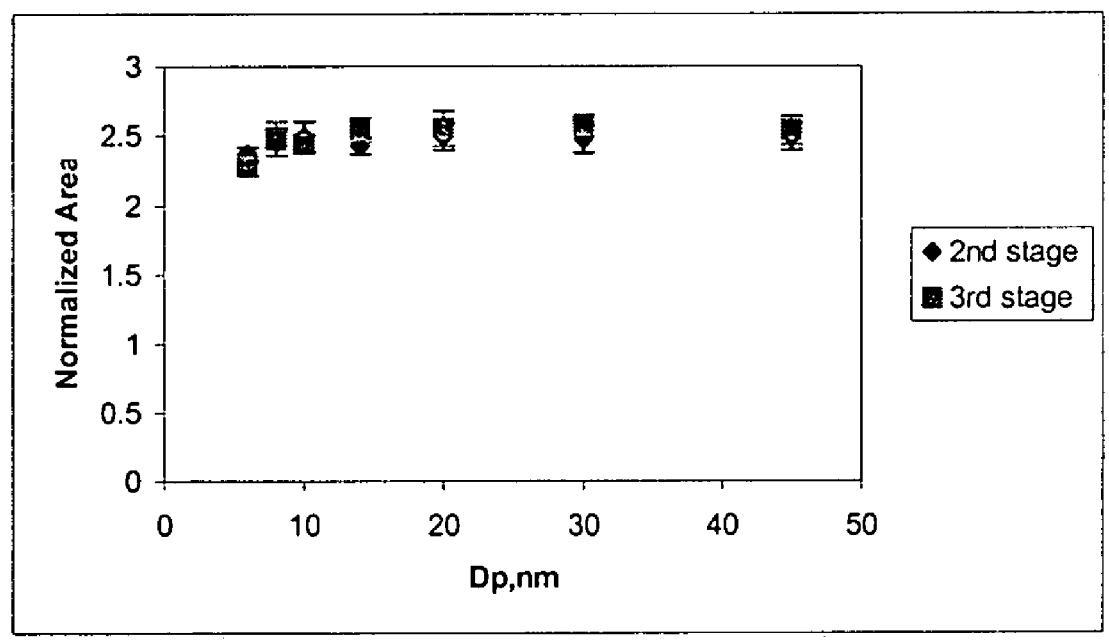

FIG. 12 shows the deconvoluted MDMA transfer function parameters (half-width and normalized area) as a function of particle size at the second and the third stage. MDMA 100 was operated at sheath flow 50 lpm, aerosol flow 4.5 lpm and aerosol sampling flow 1.5 lpm. It can be seen that the half-width reaches the theoretical value of 0.09 at the second stage for particle larger than 30 nm. The curve level off toward larger particles at the third stage. However, the half-width is greater than the theoretical value of 0.093 for the entire particle size range. The constant value approached is nearly the same as the theoretical value 0.13 at sheath flow 36 lpm while keeping the same aerosol flow and sampling flow. Possible explanations for this observation are: (1) the half-width is expected to decreases as increasing sheath flow while maintaining the other operation conditions the same; (2) Due to long classification length of third stage, flow may not be uniform any more. Turbulence flow is likely to happen along the wall at the third stage. Flow disturbance can also happen in the interface of aerosol and sheath flow. The flow imperfection may cause the broadening of the transfer function. The interaction of these two affects results in a nearly constant half-width with sheath flow ranging from 36 to 50 lpm at third stage.

Also shown in FIG. 12 is the normalized area as a function of particle size. No significant decrease is observed even for particles less than 10 nm. The flow disturbance enhance the broadening, not the diffusion loss in MDMA.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

We claim:

1. A multi-stage differential mobility analyzer (MDMA) for aerosol measurements, comprising:
   a first electrode or grid including at least one inlet or injection slit for receiving an aerosol, said aerosol including a plurality of charged particles for analysis;
   a second electrode or grid spaced apart from said first electrode, said second electrode having at least one sampling outlet disposed at a plurality different distances along its length, a volume between said first and second electrode or grid between said inlet or injection slit and a distal one of said plurality of sampling outlets forming a classifying region, said first and second electrodes for charging to suitable potentials to create an electric field within said classifying region, and
   at least one inlet or injection slit in said second electrode for receiving a sheath gas flow into an upstream end of said classifying region;
   wherein each said sampling outlets at each of said plurality of distances function as independent DMA stages and classify different size ranges of said charged particles based on electric mobility simultaneously.

2. The MDMA of claim 1, wherein said first electrode or grid is an inner electrode disposed within said second electrode.

3. The MDMA of claim 1, further comprising a flow laminarizor disposed between said inlet or injection slit for receiving said sheath gas flow and said classifying region, wherein said flow laminarizor distributes and laminates said sheath gas flow before entry into said classifying region.

4. The MDMA of claim 1, wherein said MDMA is an axially symmetric (cylindrical) MDMA.

5. The MDMA of claim 1, wherein said MDMA is a radially symmetric MDMA.

6. The MDMA of claim 1, wherein said independent DMA stages collectively and simultaneously classify particles sizes from 1 nm to up to 1000 nm.

7. The MDMA of claim 1, further comprising a condensation particle counter or induction electrometer connected to each of sampling outlet for counting a number of charged particles.

8. The MDMA of claim 1, wherein said MDMA is modularized to allow modification of a number and length of said DMA stages.

9. A method for measuring a size distribution of aerosols, comprising the steps of:
   providing a differential mobility analyzer (MDA);
   providing an aerosol including a plurality of charged particles for analysis;
   injecting said aerosol into a classifying region of said MDA bounded by a length between spaced apart and inner and outer electrodes or grids biased at a DC bias voltage to create an electric field therebetween, said outer electrode having at least one sampling outlet disposed at a plurality different distances along said length to provide a plurality of MDA stages each having different classification lengths;
   injecting a sheath gas flow into an upstream end of said classifying region;
   withdrawing sampling flow using said sampling outlets at least two of said plurality of distances, wherein different particle size peaks are withdrawn from respective ones of said sampling outlets.

10. The method of claim 9, wherein said aerosol is injected from a central inner electrode and said sampling flow is withdrawn through an outer electrode.

11. The method of claim 9, wherein said MDMA is modularized, further comprising the step of modifying a number or a length of said DMA stages.

12. The method of claim 9, further comprising the step of extracting aerosol flow from said MDA at a rate which evenly partitions a flowrate of said aerosol at each of said MDA stages.

13. The method of claim 9, further comprising the step of scanning said DC bias voltage.

14. The method of claim 9, further comprising the step of extracting aerosol flow from said MDA at a rate equal to the flowrate of said aerosol.

* * * * *